United States Patent
Anderson et al.

(10) Patent No.: US 9,073,951 B2
(45) Date of Patent: Jul. 7, 2015

(54) METHOD OF PREPARING AN ORGANOHALOSILANE

(75) Inventors: Kurt E. Anderson, Crestwood, KY (US); Aswini K. Dash, Florence, KY (US); Charles Alan Hall, Crestwood, KY (US); Dimitris Katsoulis, Midland, MI (US); Robert Thomas Larsen, Midland, MI (US); Matthew J. McLaughlin, Midland, MI (US); Jonathan David Wineland, Bedford, KY (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/575,345

(22) PCT Filed: Jan. 24, 2011

(86) PCT No.: PCT/US2011/022195
§ 371 (c)(1),
(2), (4) Date: Jul. 26, 2012

(87) PCT Pub. No.: WO2011/094140
PCT Pub. Date: Aug. 4, 2011

(65) Prior Publication Data
US 2012/0289730 A1 Nov. 15, 2012

Related U.S. Application Data

(60) Provisional application No. 61/298,375, filed on Jan. 26, 2010.

(51) Int. Cl.
*C07F 7/12* (2006.01)
*C07F 7/16* (2006.01)

(52) U.S. Cl.
CPC ...................................... *C07F 7/16* (2013.01)

(58) Field of Classification Search
USPC .................. 556/478, 472, 450; 502/178, 185
See application file for complete search history.

(56) References Cited

U.S. PATENT DOCUMENTS

| | | | |
|---|---|---|---|
| 2,403,370 | A | 7/1946 | Hurd |
| 2,888,476 | A | 5/1959 | Little et al. |
| 3,057,686 | A | 10/1962 | Muetterties |
| 4,314,908 | A | 2/1982 | Downing et al. |
| 4,526,769 | A | 7/1985 | Ingle et al. |
| 4,836,997 | A | 6/1989 | Lepage et al. |
| 4,888,435 | A | 12/1989 | Chadwick et al. |
| 4,946,980 | A | 8/1990 | Halm et al. |
| 4,956,326 | A * | 9/1990 | Yoneda et al. ............... 502/178 |
| 4,973,725 | A | 11/1990 | Lewis et al. |
| 5,716,590 | A | 2/1998 | Roewer et al. |
| 6,156,380 | A | 12/2000 | Aramata et al. |
| 6,211,284 | B1 | 4/2001 | Ishikawa et al. |
| 6,326,452 | B1 * | 12/2001 | Berrier et al. ............... 528/12 |
| 6,790,749 | B2 | 9/2004 | Takemura et al. |
| 6,887,448 | B2 | 5/2005 | Block et al. |
| 7,208,617 | B2 | 4/2007 | Gammie |
| 7,223,879 | B2 | 5/2007 | Buchwald et al. |
| 7,442,824 | B2 | 10/2008 | Paetzold et al. |
| 7,716,590 | B1 | 5/2010 | Nathan |
| 8,697,900 | B2 | 4/2014 | Anderson et al. |
| 8,772,525 | B2 | 7/2014 | Katsoulis et al. |
| 2002/0156310 | A1 * | 10/2002 | Inukai et al. ............... 556/472 |
| 2005/0074387 | A1 | 4/2005 | Bulan et al. |
| 2005/0220514 | A1 | 10/2005 | Hisakuni |

FOREIGN PATENT DOCUMENTS

| | | |
|---|---|---|
| CA | 2829701 A1 | 9/2012 |
| DE | 3024319 | 1/1982 |
| DE | 4041644 A1 | 6/1992 |
| DE | 19654154 | 6/1997 |
| JP | S28-000669 | 2/1953 |
| JP | 51-23226 | 2/1976 |
| JP | 2009111202 | 5/2009 |
| WO | 0248034 | 6/2002 |
| WO | 2005051963 | 6/2005 |

(Continued)

OTHER PUBLICATIONS

Beccalli, Egle M., et al., C—C, C—O, C—N Bond Formation on sp2 Carbon by Palladium(II)-Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.

Methivier, et al., Pd/SiC catalysts. Characterization and catalytic activity for the methane total oxidation.. Institut de Recherches sur la Catalyse—CNRS, conventionne a l'Universite Claude Bernard Lyon 1, Villeurbanne, Fr. Journal of Catalysis (1998), 173(2), 374-382.

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

Tanaka, Miyoko et al., Nanomaterials Laboratory, National Institute for Materials Science, Tsukuba, Sakura, Japan. Journal of Crystal Growth (2002), 237-239(Pt. 1), 254-258.

(Continued)

*Primary Examiner* — Sudhakar Katakam
*Assistant Examiner* — Pancham Bakshi
(74) *Attorney, Agent, or Firm* — Catherine U. Brown; Matthew T. Fewkes

(57) ABSTRACT

A method of preparing organohalosilanes comprising combining an organohalide having the formula RX (I), wherein R is a hydrocarbyl group having 1 to 10 carbon atoms and X is fluoro, chloro, bromo, or iodo, with a contact mass comprising at least 2% (w/w) of a palladium suicide of the formula $Pd_xSi_y$ (II), wherein x is an integer from 1 to 5 and y is 1 to 8, or a platinum suicide of formula $Pt_zSi$ (III), wherein z is 1 or 2, in a reactor at a temperature from 250 to 700° C. to form an organohalosilane.

15 Claims, No Drawings

(56) References Cited

FOREIGN PATENT DOCUMENTS

| WO | 2009037301 | 3/2009 |
|---|---|---|
| WO | 2012-123159 | 9/2012 |
| WO | 2014028417 A2 | 2/2014 |
| WO | 2014062255 A1 | 4/2014 |

OTHER PUBLICATIONS

Terao, Jun et al., Transition metal-catalyzed C—C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon—carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

Dallas T. Hurd, The Vapor Phase Alkylation and Hydrogenation of Chlorosilanes, J. Am. Chem. Soc., 1945, 67 (9), pp. 1545-1548.

Eaborn, C. et al., Further studies on reactions of organic halides with disilanes catalysed by transition metal complexes, Journal of Organometallic Chemistry, vol. 225, 1982, pp. 331-341.

Golubtsov, S.A. et al., Role of the Products of Partial Chlorination of Silicon in the Formation of Methyltrichlorosilane, Russian Chemical Bulletin, vol. 21, No. 3 (1972), pp. 584-586.

H. Walter, Mechanism of the silicide-catalysed hydrodehalogenation of silicon tetrachloride to trichlorosilane, J. Chem. Soc., Faraday Trans., 1996,92, 4605-4608.

Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.

Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.

Lobusevich, N.P. et al., Reactions During Direct Synthesis of Alkylchlorosilanes., vol. 48, No. 11, 1978, pp. 2534-2541.

Moreno-Manas, Marcial et al., Formation of Carbon—Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

Acker, et. al., "Reactivity of Intermetallic Compounds: A Solid State Approach to Direct Reactions of Silicon", J. Phys. Chem., 2002, pp. 5105-5117, vol. 106, Freiberg, Germany.

Acker, et. al., "Thermodynamic assessment of the copper catalyzed direct synthesis of methylchlorosilanes", Journal of Organometallic Chemistry, 2008, pp. 2483-2493, vol. 693, Freiberg, Germany.

\* cited by examiner

US 9,073,951 B2

METHOD OF PREPARING AN ORGANOHALOSILANE

CROSS REFERENCE TO RELATED APPLICATIONS

This application is a U.S. national stage filing under 35 U.S.C. §371 of PCT Application No. PCT/US11/022,195 filed on Jan. 24, 2011, currently pending, which claims the benefit of U.S. Provisional Patent Application No. 61/298,375 filed Jan. 26, 2010 under 35 U.S.C. §119 (e). PCT Application No. PCT/US11/022,195, U.S. Provisional Patent Application No. 61/298,375 are hereby incorporated by reference.

FIELD OF THE INVENTION

The present invention relates to a method of preparing an organohalosilane, comprising combining an organohalide having the formula RX (I) with a contact mass to form an organohalosilane, wherein R is a hydrocarbyl group, X is a halo group, and the contact mass comprises at least 2% (w/w) of a palladium or platinum silicide.

BACKGROUND OF THE INVENTION

Methods of preparing organohalosilanes are known in the art. Typically, organohalosilanes are produced commercially by the Mueller-Rochow Direct Process, which comprises passing an organohalide over zero-valent silicon in the presence of a copper catalyst and various optional promotors. A mixture of organohalosilanes, the most important of which is dimethyldichlorosilane, are produced by the Direct Process.

The typical process for making the zero-valent silicon used in the Direct Process consists of the carbothermic reduction of $SiO_2$ in an electric arc furnace. Extremely high temperatures are required to reduce the $SiO_2$, so the process is very energy intensive. Consequently, production of zero-valent silicon adds costs to the Direct Process for producing organohalosilanes. Therefore, there is a need for a more economical method of producing organohalosilanes that avoids or reduces the need of using zero-valent silicon.

BRIEF SUMMARY OF THE INVENTION

The present invention is directed to a method of preparing an organohalosilane, the method comprising combining an organohalide having the formula RX (I), wherein R is a hydrocarbyl group having 1 to 10 carbon atoms and X is fluoro, chloro, bromo, or iodo, with a contact mass comprising at least 2% (w/w) of a palladium silicide of the formula $Pd_xSi_y$ (II), wherein x is an integer from 1 to 5 and y is and integer from 1 to 8, or a platinum silicide of formula $Pt_zSi$ (III), wherein z is 1 or 2, in a reactor at a temperature from 250 to 700° C. to form an organohalosilane.

The method of the present invention produces an organohalosilane from a silicon source other than zero-valent silicon. The organohalosilane produced by the present method is the precursor of many products in the silicone industry. For example, the organohalosilane is the precursor used to make many silicone fluids and resins.

DETAILED DESCRIPTION OF THE INVENTION

As used herein, the term "a" or "an" means one or more.
As used herein, "integer" means a natural number and zero.

As used herein, the meaning of "combine," "combined," and "combining" is intended to include, but is not limited to, the meaning "to cause to react or unite."

A method of preparing an organohalosilane, comprising:
combining an organohalide having the formula RX (I), wherein R is a hydrocarbyl group having 1 to 10 carbon atoms and X is fluoro, chloro, bromo, or iodo, with a contact mass comprising at least 2% (w/w) of a palladium silicide of the formula $Pd_xSi_y$ (II), wherein x is an integer from 1 to 5 and y is and integer from 1 to 8, or a platinum silicide of formula $Pt_zSi$ (III), wherein z is 1 or 2, in a reactor at a temperature from 250 to 700° C. to form an organohalosilane.

The organohalide has the formula RX (I), wherein R is hydrocarbyl group having 1 to 10 carbon atoms and X is fluoro, chloro, bromo, or iodo.

The hydrocarbyl groups represented by R in formula (I) typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and naphthyl; alkaryl, such as tolyl, and xylyl; aralkyl such as benzyl and phenylethyl; alkenyl, such as vinyl, allyl, and propenyl; aralkenyl, such as styryl and cinnamyl; and alkynyl, such as ethynyl and propynyl.

Examples of organohalides include, but are not limited to, methyl chloride, methyl bromide, methyl iodide, ethyl chloride, ethyl bromide, ethyl iodide, chlorobenzene, bromobenzene, iodobenzene, vinyl chloride, vinyl bromide, vinyl iodide, allyl chloride, allyl bromide, and ally iodide.

Methods of preparing organohalides are well known in the art; many of these compounds are commercially available.

The contact mass comprises at least 2% (w/w), alternatively at least 25% (w/w), alternatively at least 50% (w/w), alternatively at least 75% (w/w), alternativley at least 90% (w/w), alternatively at least 95% (w/w), alternatively about 100% (w/w), based on the total weight of the contact mass, of a palladium silicide of the formula $Pd_xSi$ (II), wherein x is an integer from 1 to 5, or a platinum silicide of formula $Pt_zSi$ (III), wherein z is 1 or 2.

The palladium silicide has the formula $Pd_xSi_y$ (II), wherein x is an integer from 1 to 5, alternatively x is 1, 2, 3, or 5, alternatively x is 1 or 2, alternatively x is 2, and y is and integer from 1 to 8, alternatively y is 1 when x is 1, 3, 4, or 5 and y is 1 or 8 when x is 2; alternatively y is 1.

Examples of palladium silicides include, but are not limited to, PdSi, $Pd_2Si$, $Pd_3Si$, $Pd_5Si$, and $Pd_2Si_8$. The palladium silicide may be a single palladium silicide or a mixture of palladium silicides, each having the formula (II).

Palladium silicides may be made by methods well known in the art. For example, the methods disclosed in U.S. Pat. No. 3,297,403 and US 2009/0275466 may be used. The palladium silicide may be obtained commercially from, for example, Alfa Aesar and ACI Alloy.

The platinum silicide has the formula $Pt_zSi$ (III), wherein z is 1 or 2. Examples of platinum silicides include PtSi and $Pt_2Si$. The platinum silicide may be a single platinum silicide or a mixture of PtSi and $Pt_2Si$.

Platinum silicides may be made by methods well known in the art as described above for the palladium silicide. The platinum silicide may be obtained commercially from, for example, Alfa Aesar and ACI Alloy.

The contact mass may comprise a mixture of palladium silicides, a mixture of platinum silicides or a mixture of palladium and platinum silicides. For example, the contact mass may be a mixture of PdSi and $Pd_2Si$ or of $Pt_2Si$ and PtSi.

The contact mass may further comprise up to 98% (w/w), alternatively up to 75% w/w), alternatively up to 50% (w/w), alternatively up to 25% (w/w), alternatively up to 10% (w/w), alternatively up to 5% (w/w), based on the total weight of the contact mass, zero-valent silicon. In a another embodiment, the contact mass comprises essentially no zero-valent silicon. As used herein, "essentially no zero-valent silicon" is intended to mean that there is no zero-valent silicon other than at the level of an impurity. For example, essentially no zero-valent silicon means that there is from 0 to 1% (w/w), alternatively 0 to 0.5% (w/w), alternatively 0% (w/w), based on the total weight of the contact mass, zero-valent silicon.

The zero-valent silicon is typically chemical or metallurgical grade silicon; however, different grades of silicon, such as solar or electronic grade silicon may be used. Chemical and metallurgical grades of silicon are known in the art and can be defined by the silicon content. For example, chemical and metallurgical grades of silicon typically comprise at least 98.5% (w/w) silicon. Chemical and metallurgical grades of silicon may also contain additional elements as described below for the contact mass. Methods of making zero-valent silicon are known in the art. These grades of silicon are available commercially.

The contact mass may comprise other elements such as Fe, Ca, Ti, Mn, Zn, Sn, Al, Pb, Bi, Sb, Ni, Cr, Co, and Cd and their compounds. Each of these elements are typically present at from 0.0005 to 0.6% (w/w) based upon the total weight of the contact mass.

The contact mass may be a variety of forms, shapes and sizes, up to several centimeters in diameter, but the contact mass is typically finely-divided. Finely divided, as used herein, is intended to mean that the contact mass is in the form of a powder.

The contact mass may be produced by standard methods for producing particulate silicon from bulk silicon, such as silicon ingots. For example, attrition, impact, crushing, grinding, abrasion, milling, or chemical methods may be used. Grinding is typical. The contact mass may be further classified as to particle size distribution by means of, for example, screening or by the use of mechanical aerodynamic classifiers such as a rotating classifier.

If the contact mass comprises more than a single silicide, for example if the contact mass comprises at least two silicides or a silicide and zero-valent silicon, these components typically are mixed. The mixing may be accomplished by standard techniques known in the art for mixing solid particles. For example, the mixing may be accomplished by stirring or shaking. Further, mixing may be accomplished in the processing to produce the contact mass particle size mass distribution as described and exemplified above. For example, mixing may be accomplished in a grinding process. Still further, the mixing may be accomplished during the production of the palladium silicide or platinum silicide. For example, PdSi and $Pd_2Si$ may be formed and mixed in the process combining molten silicon with molten palladium.

The method of the invention can be carried out in a suitable reactor for conducting the Direct Process. For example, a sealed tube, an open tube, a fixed bed, a stirred bed, and a fluidized bed reactor may be used.

The organohalide and contact mass are typically combined by charging the reactor with the contact mass followed by flowing the gaseous organohalide through the contact mass; however, the reactor may be first charged with the organohalide followed by introduction of the contact mass.

The rate of addition of the organohalide to the contact mass is not critical; however, when using a fluidized bed, the organohalide is introduced into the reactor bed at a rate sufficient to fluidize the bed but below a rate that will completely elutriate the bed. The rate will depend upon the particle size mass distribution of the particles in the bed and the dimensions of the fluidized bed reactor. One skilled in the art would know how to determine a sufficient rate of organohalide addition to fluidize the bed while not completely elutriating the material from the bed. When not using a fluidized bed, the rate at which the organohalide is added to the bed is typically selected to optimize contact mass reactivity.

The method may further comprise combining the organohalide and contact mass in the presence of an inter gas. For example, an inert gas may be added with the organohalide to the contact mass. Examples of the inert gas that may be introduced with the organohalide include nitrogen, helium, argon and mixtures thereof.

The method may be conducted with agitation of the reactants. Agitation may be accomplished by methods known in the art for catalyzed reactions between gases and solids. For example, reaction agitation may be accomplished within a fluidized bed reactor, in a stirred bed reactor, a vibrating bed reactor and the like. However, the method may be conducted without agitation of the reactants by, for example, flowing the alkyl halide as a gas over a packed bed comprising the palladium or platinum silicide.

The method may be carried out at atmospheric pressure conditions, or slightly above atmospheric pressure conditions, or elevated pressure conditions may be used.

The temperature at which the contact mass and organohalide are combined is from 250 to 750° C., alternatively 280 to 700° C., alternatively 300 to 700° C., alternatively from 400 to 700° C. The temperature at which the contact mass and organohalide are combined influences the selectivity of the method for producing monoorganohalosilane or diorganohalosilane. The selectivity may be determine by gas chromatography as defined in the examples section, or through other suitable analytical techniques.

The contact mass and organohalide are typically combined for sufficient time to form organohalosilanes from the reaction of the palladium or platinum silicide with the organohalide. For example, in a batch-type reactor, the contact mass and organohalide are typically combined from 5 minutes to 24 h, alternatively from 1 to 7 h, alternatively from 4 to 7 h, at a temperature from 300 to 700° C. In a continuous or semi-continuous process, where additional contact mass may be added to the reactor, and organohalide gas is continuously passed through the contact mass, the contact time is typically from a fraction of a second up to 30 seconds, alternatively from 0.01 to 15 seconds, alternatively from 0.05 to 5 seconds. As used herein, "contact time" is intended to mean the residence time of gas to pass through the reactor.

When the organohalide is a liquid or solid, the method may further comprise pre-heating and gasifying the organohalide before it is introduced into the reactor.

The method may further comprise pre-heating the contact mass in an inert atmosphere and at a temperature up to 700° C., alternatively up to 400° C., alternatively 280 to 525° C., prior to contacting with the organohalide.

The method may further comprise introducing additional contact mass or zero-valent silicon into the reactor to replace the silicon that has reacted with the organohalide to form organohalosilanes.

The method may further comprise recovering the organohalosilane produced. The organohalosilane may be recovered by, for example, removing gaseous organohalosilane from the reactor followed by condensation. The organohalosilane may be recovered and a mixture of organohalosilanes separated by distillation.

The organohalosilanes prepared according to the present method typically have the formula $R_aSiX_{4-a}$, wherein each R is independently H or as described and exemplified above for the organohalide and X is as described and exemplified above for the organohalide, and the subscript "a" is an integer from 1 to 3.

Examples of organohalosilanes prepared according to the present method include, but are not limited to, dimethyldichlorosilane (i.e., $(CH_3)_2SiCl_2$), dimethyldibromosilane, diethyldichlorosilane, diethyldibromosilane, trimethylchlorosilane (i.e., $(CH_3)_3SiCl$), methyltrichlorosilane (i.e., $(CH_3)SiCl_3$), phenyltrichlorosilane, diphenyldichlorosilane, triphenylchlorosilane, and methylhydrodichlorsilane (i.e., $(CH_3)HSiCl_2$). The method may also produce small amounts of halosilane and organosilane products such as tetramethylsilane, trichlorosilane, and tetrachlorosilane.

The method of the present invention produces organohalosilanes from a silicon source other than zero-valent silicon, does not require the addition of copper as catalyst, and produces commercially desirable organohalosilanes in good yield and proportion to less desirable silanes.

The organohalosilanes produced by the present method are the precursors of most of the products in the silicone industry. For example, dimethyldichlorosilane may be hydrolyzed to produce linear and cyclic polydimethylsiloxanes. Other organohalosilanes produced by the method may also be used to make other silicon-containing materials such as silicone resins or sold into a variety of industries and applications.

EXAMPLES

The following examples are presented to better illustrate the method of the present invention, but are not to be considered as limiting the invention, which is delineated in the appended claims. Unless otherwise noted, all parts and percentages are reported in the examples are by weight. The following methods and materials were employed in the examples:

The reaction products were analyzed by gas chromatography-mass spectrometry using a Agilent Technologies 6890N Network GC system with 5975B inert XL EI/CI MSD (GC-MS) to determine selectivity.

Concentration of silicon and other elements were determined by inductively coupled plasma—atomic emission spectrometry (ICP-AES). The method was a typical procedure known for elemental analysis of solid samples, wherein the solids were dissolved in HF and the concentration in aqueous solution determined with respect to appropriate standards containing known amounts of any elements of interest.

Methyl iodide (99+%), deuterated-methyl iodide (99+%), and methyl bromide (99+%) are available from Sigma-Aldirch (Milwaukee, Wis.). Methyl chloride (>99.9% (w/w)) purity is available from Airgas. The palladium and platinum silicides are available from Alfa Aesar (Ward Hill, Mass.) and ACI Alloy (San Jose, Calif.).

The flow-through, metal reactor tube set-up consisted of a 0.25 inch stainless steel tube placed either vertically or horizontally. The silicide to be tested was positioned in the middle of the tube, and the organohalide was introduced from the top end of the vertically aligned tube and from one of the ends of the horizontally aligned tubes. The product and unreacted organohalide were removed from the end of the tube opposite the organohalide introduction and passed through a cold trap at −78° C. The organohalide is fed to the reactor from a gas cylinder via a mass controller.

Silicon Conversion is the starting weight of silicon before reaction minus the weight of silicon remaining after the reaction divided by the starting weight of the silicon before the reaction multiplied by 100.

As used herein, "h" is the abbreviation for hour or hours, "g" is the abbreviation for gram or grams, "mg" is the abbreviation for milligram or milligrams, "min" is the abbreviation for minute or minutes, "mL" is the abbreviation for milliliters, and "μL" is the notation for microliters.

Example 1

A thick-wall glass reactor tube was charged with a sample of PdSi (110 mg) and methyl iodide (75 μL) at 23° C. The tube was evacuated at −196° C., sealed and then warmed to room temperature. The tube was than placed in an oven at 300° C. After 2 h, the temperature of the reactor tube was allowed to reach 23° C. and then was frozen with liquid nitrogen (−196° C.). Using a triangular file, the tube was cut, warmed to room temperature and then a liquid sample was collected for analysis. The sample was injected directly for analysis by gas chromatography-mass spectrometry and showed the selective formation of $MeSiI_3$ as the only organohalosilane.

Example 2

A thick-wall glass reactor tube was charged with a sample of PdSi (110 mg) and methyl iodide (75 μL) at 23° C. The tube was evacuated at −196° C., sealed and then warmed to room temperature. The tube was kept in an oven and heated at 300° C. After 5 h, the temperature of the reactor tube was allowed to cool to 23° C. and then was frozen with liquid nitrogen (−196° C.). Using a triangular file, the tube was cut, warmed to room temperature and then a sample of the liquid product was collected for analysis. The sample was injected directly for analysis by gas chromatography-mass spectrometry and showed the selective formation of the organohalosilanes $MeSiI_3$ and $Me_2SiI_2$. A trace amount of $SiI_4$ was also detected. The selectivity among organohalosilanes observed was $MeSiI_3$ (72% (w/w)), $Me_2SiI_2$ (26% (w/w)) and $SiI_4$ (2% (w/w)).

Example 3

An open-ended, glass tube was loaded with 500 mg of PdSi. The tube was heated to 330° C. with an aluminum heating block. MeBr was pumped through the tube for 7 h. Reaction products were collected in a cold trap downstream of the tube. Headspace gas chromatography-mass spectrometry analysis was performed on the vial containing the liquid collected. The major products were $Me_2SiBr_2$ and $MeSiBr_3$. A number of other organohalosilanes and siloxanes were seen in small amounts.

Example 4

A sample of PdSi (2.018 g) was loaded into a glass reactor tube and pretreated with argon overnight. Next, MeCl (6 mL/min) was flowed through the PdSi at from 200-500° C. for 2.5 h, and the product stream was analyzed by online GC. At 300° C., the product stream contained 50/50% (w/w) $SiCl_4$/$MeSiCl_3$; at 400° C., the product stream contained 50/50%

(w/w) $SiCl_4/Me_2SiCl_2$; and at 500° C., and the product stream contained 80/10/10% (w/w) $MeSiCl_3/SiCl_4/Me_2SiCl_2$.

Example 5

A sample of PdSi (150.0 mg) was loaded into the flow-through, metal reactor and pretreated with nitrogen at 150° C. overnight. Next, MeCl (30 mL/min) was flowed through the PdSi at 400° C. for 7 h. The remaining solids left in the tube were analyzed by ICP-AES and showed Si conversion of 35% (w/w). The products were analyzed by GC and found to contain $Me_2SiCl_2$ (31% (w/w)), $MeSiCl_3$ (58% (w/w)), and $SiCl_4$ (11% (w/w)).

Example 6

A sample of $Pd_2Si$ (200.0 mg) was loaded into a flow-through, metal reactor and pretreated with nitrogen at 150° C. overnight. Next, MeCl (30 mL/min) was flowed through the catalyst bed continuously at 400° C. for 4 h, 450° C. for 1.5 h, and 500° C. for 2 h. The remaining solids left in the tube were analyzed by ICP-AES, and the Si conversion was determined to be 82.8% (w/w). $MeSiCl_3$ was the only organohalosilane in the product as measured by GC.

Example 7

PtSi (0.5 g) was loaded in a flow-through, metal reactor and pretreated with nitrogen at 150° C. overnight. Next, MeCl (30 mL/min) was flowed through the catalyst bed at 500° C. for 2 h. GC analysis showed the product formed comprised $Me_2SiCl_2$ and $MeSiCl_3$.

Example 8

A sample of $Pd_3Si$ (500.0 mg) was loaded into the flow-through, metal reactor and pretreated with nitrogen at 150° C. overnight. Next, MeCl (30 mL/min) was flowed through the $Pd_3Si$ bed and the evolution of products at 400-700° C. were analyzed by combination of GC and GC-MS techniques. No volatile organohalosilane products were observed at 400-600° C. At 700° C., product comprising $SiCl_4$ (68%) and $MeSiCl_3$ (31%) was produced. The reaction was continued at 700° C. for another 30 min resulting in product comprising $SiCl_4$ (97%) and $MeSiCl_3$ (3%).

Example 9

A sample of $Pd_5Si$ (500.0 mg) was loaded into the flow-through, metal reactor and pretreated with nitrogen at 150° C. overnight. Next, MeCl (30 mL/min) was flowed through the $Pd_5Si$ bed varying the temperature from 400 to 700° C., and the products were analyzed by GC and GC-MS. No volatile organohalosilane products were observed at 400-500° C. At 600° C., $SiCl_4$ (62%) and $MeSiCl_3$ (38%) were observed. After 30 min at 700° C., product comprising $SiCl_4$ (77%) and $MeSiCl_3$ (23%) was produced; and after 60 min at 700° C., product comprising $SiCl_4$ (97%) and $MeSiCl_3$ (3%) was produced.

Example 10

A sample of $Pd_2Si_8$ (0.51 g) was loaded into the flow-through, metal reactor. MeCl was flowed through the $Pd_2Si_8$ bed at 400° C. and 500° C., and the products were analyzed by GC and GC-MS. At 400° C., 9.5% (w/w) $Me_2SiCl_2$, 59.3% (w/w) $MeSiCl_3$, and 30.4% (w/w) $SiCl_4$ were produced, and at 500° C., 2.1% $MeHSiCl_2$, 1.7% $Me_2SiCl_2$, 29.2% $MeSiCl_3$, 0.5% $HSiCl_3$, 66.2% $SiCl_4$, with the balance being other silanes, were produced.

Example 11

A sample of PdSi and zero-valent Si, at a weight ratio of PdSi to zero-valent Si of 1:22, was loaded into a flow-through, metal reactor. MeCl was flowed through at a temperature of 400° C. for 24 hr. The products leaving the reactor were analyzed by GC and GC-MS after 6 and 24 hr. After 6 hours, 76% (w/w) $MeHSiCl_2$, 4% (w/w) $Me_2SiCl_2$, 17% (w/w) $MeSiCl_3$ were produced, and 62% (w/w) $MeHSiCl_2$, and 16% (w/w) $Me_2SiCl_2$ after 24 hr, with the balance being other silanes, were produced. The total Si conversion was 2.4%.

Example 12

A sample of PdSi (500.0 mg) was loaded into a flow-through, metal reactor and treated with nitrogen at 150° C. overnight. Next, MeCl (30 mL/min) was flowed through the PdSi bed at 400° C. for 2 h. The products were analyzed by GC and found to contain $Me_2SiCl_2$ (73.5% (w/w)), and $MeSiCl_3$ (26.5% (w/w)).

Example 13

A sample of PdSi (500.0 mg) was loaded into a flow-through, metal reactor and treated with nitrogen at 150° C. overnight. Next, MeCl (30 mL/min) was flowed through the PdSi bed at 400° C. for 4 h. The products were analyzed by GC and found to contain $Me_2SiCl_2$ (57.3% (w/w)), and $MeSiCl_3$ (42.7% (w/w)). Si conversion was 5.6%.

Example 14

A sample of PdSi (500.0 mg) was loaded into a flow-through, metal reactor and treated with nitrogen at 150° C. overnight. Next, MeCl (30 mL/min) was flowed through the PdSi bed at 400° C. for 6 h. The products were analyzed by GC and found to contain $Me_2SiCl_2$ (46.5% (w/w)), and $MeSiCl_3$ (53.5% (w/w)). Si conversion was 8.5%.

Example 15

A sample of grinded PdSi (500.0 mg; particle size <50 micron) was loaded into a flow-through, metal reactor and treated with nitrogen at 150° C. overnight. Next, MeCl (30 mL/min) was flowed through the PdSi bed at 400° C. for 5 h. The products were analyzed by GC and found to contain $MeHSiCl_2$ (2.0%(w/w)), $SiCl_4$ (10.2% (w/w)), $Me_2SiCl_2$ (14.8% (w/w)), $MeSiCl_3$ (72.3% (w/w)) and $(MeO)SiCl_3$ (0.5% (w/w)). Si conversion was 14.0%.

Comparative Example 1

An open-ended, glass tube was loaded with NiSi (0.5 g). The tube was heated to 330° C. with an aluminum heating block, and MeBr was then pumped through the tube for 7 h. There were no organohalosilanes detected by GC-MS in the material collected in a downstream cold trap at −78° C.

Comparative Example 2

An open-ended, glass tube was loaded with $CoSi_2$ (0.5 g). The sample was pretreated with $N_2$ at 250° C. for 45 min, and then MeCl (25-40 mL/min) was flowed through the system at 330° C. for 3-5.5 h. No liquids were collected in a downstream cold trap (−78° C.). There were no organohalosilanes detected.

Comparative Example 3

An open-ended, glass tube was loaded with $CrSi_2$ (0.5 g). The sample was pretreated with $N_2$ at 250° C. for 45 min, and MeCl (25-40 mL/min) was then flowed through the system at 330° C. for 3-5.5 h. No liquids were collected in a downstream cold trap (−78° C.), and no organohalosilanes were detected by GC-MS.

Comparative Example 4

An open-ended, glass tube was loaded with $WSi_2$ (0.5 g). The sample was pretreated with $N_2$ at 250° C. for 45 min, and MeCl (25-40 mL/min) was then flowed through the system at 330° C. for 3-5.5 h. No liquids were collected in a downstream cold trap (−78° C.), and no organohalosilanes were detected by GC-MS.

Comparative Example 5

An open-ended, glass tube was loaded with $TaSi_2$ (0.5 g). The sample was pretreated with $N_2$ at 250° C. for 45 min, and MeCl (25-40 mL/min) was then flowed through the system at 330° C. for 3-5.5 h. No liquids were collected in a downstream cold trap (−78° C.), and no organohalosilanes were detected by GC-MS.

Comparative Example 6

A thick-wall glass reactor tube was charged with a sample of NiSi (110 m) and methyl iodide (75 μL) at 23° C. The tube was evacuated at −196° C., sealed, and then warmed to room temperature. The tube was kept in an oven and heated at 300° C. After 5 h, the temperature of the reactor tube was allowed to reach 23° C. and then was frozen with liquid nitrogen (−196° C.). Using a triangular file, the tube was cut, warmed to room temperature, and then a liquid sample was collected for analysis. A direct liquid sample injection was made on gas chromatography-mass spectrometry and no organohalosilanes were detected.

Comparative Example 7

A sample of $Pd_9Si_2$ (500.0 mg) was loaded into the flow-through, metal reactor and pretreated with nitrogen at 150° C. overnight. Next, MeCl (30 mL/min) was flowed through the $Pd_9Si_2$ bed, and the products evolving at from 400-600° C. were analyzed by GC-MS. No organohalosilanes were detected. At 600-700° C., evolution of only $SiCl_4$ was observed.

That which is claimed is:

1. A method of preparing an organohalosilane, the method comprising:
combining an organohalide having the formula RX (I), wherein R is a hydrocarbyl group having 1 to 10 carbon atoms and X is fluoro, chloro, bromo, or iodo, with a contact mass comprising at least 2% (w/w) of a palladium silicide of the formula $Pd_xSi_y$ (II), wherein x is an integer from 1 to 5 and y is an integer 1 to 8, or a platinum silicide of formula $Pt_zSi$ (III), wherein z is 1 or 2, in a reactor at a temperature from 250 to 750° C. to form an organohalosilane.

2. The method of claim 1, wherein the hydrocarbyl group has 1 to 6 carbon atoms and X is chloro.

3. The method of claim 1, wherein the organohalide is methyl chloride, methyl bromide, or methyl iodide.

4. The method of claim 1, wherein the contact mass comprises at least 90% (w/w) of a silicide selected from PdSi, $Pd_2Si$, $Pd_3Si$, $Pd_5Si$, $Pd_2Si_8$, PtSi, and $Pt_2Si$.

5. The method of claim 1, wherein the silicide is selected from PdSi, $Pd_2Si$, $Pd_2Si_8$ and PtSi.

6. The method of claim 1, wherein the reactor is selected from a fluidized bed reactor, a vibrating bed reactor, and a stirred bed reactor.

7. The method of claim 1, wherein the organohalosilane has the formula $R_aSiX_{4-a}$, wherein each R is independently H or a hydrocarbyl group having 1 to 10 carbon atoms; X is fluoro, chloro, bromo, or iodo; and a is an integer from 1 to 3.

8. The method of claim 7, wherein R is methyl and X is chloro.

9. The method of claim 1, further comprising recovering the organohalosilane.

10. The method of claim 1, further comprising replenishing the reactor with a zero-valent silicon or contact mass after the organohalosilane has been produced.

11. The method of claim 1, wherein the contact mass comprises essentially no zero-valent silicon.

12. The method of claim 1, wherein the temperature is from 250 to 700° C.

13. The method of claim 1, further comprising pre-heating and gasifying the organohalide before combining with the contact mass.

14. The method of claim 1, further comprising pre-heating the contact mass in an inert atmosphere and at a temperature up to 700° C. prior to combining with the organohalide.

15. A method of preparing a polysiloxane, the method comprising hydrolyzing the organosilane produced according to the method of claim 1.

* * * * *